United States Patent [19]

Mintz

[11] Patent Number: 4,799,488

[45] Date of Patent: Jan. 24, 1989

[54] MOVEABLE BLOTTER APPARATUS AND METHOD FOR USE IN BLEEDING-TIME TESTS

[75] Inventor: Michael D. Mintz, Edison, N.J.

[73] Assignee: International Technidyne Corporation, Edison, N.J.

[21] Appl. No.: 151,067

[22] Filed: Feb. 1, 1988

[51] Int. Cl.$^4$ .............................................. A61B 5/00
[52] U.S. Cl. .................................... 128/637; 128/638
[58] Field of Search ............... 128/DIG. 22, 637, 638, 128/770, 767, 760, 759, 170; 34/95.3

[56] References Cited

FOREIGN PATENT DOCUMENTS 964072 7/1964 United Kingdom ................ 128/637

*Primary Examiner*—William E. Kamm
*Assistant Examiner*—Timothy G. Philips
*Attorney, Agent, or Firm*—Arthur L. Plevy

[57] ABSTRACT

There is disclosed apparatus for use in bleeding-time tests. The apparatus includes an envelope which has an internal hollow and is sealed at all sides and has an opening at one side or at one corner. The envelope contains a blotter member which is located in the hollow of the envelope and dimensioned so that a peripheral section of the blotter member extends from the opening. In this manner a user can move the blotter member with respect to the envelope to thereby change the section of the blotter member which extends from the opening. The apparatus and methods enable one to utilize different sections of the blotter while directing previous blotted blood sections into the internal hollow of the envelope thereby avoiding contact with the previously blotted sections.

10 Claims, 1 Drawing Sheet

U.S. Patent  Jan. 24, 1989  4,799,488
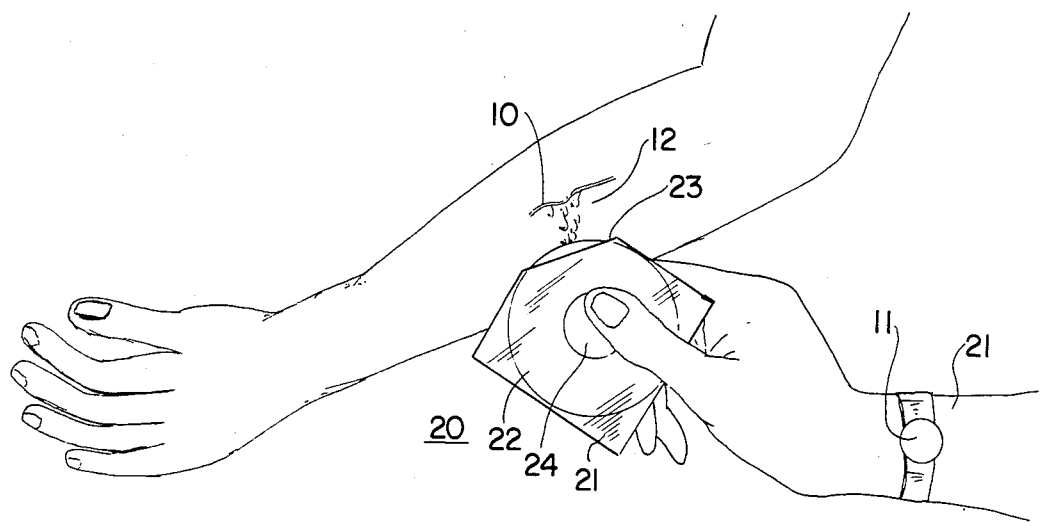
F I G. 1
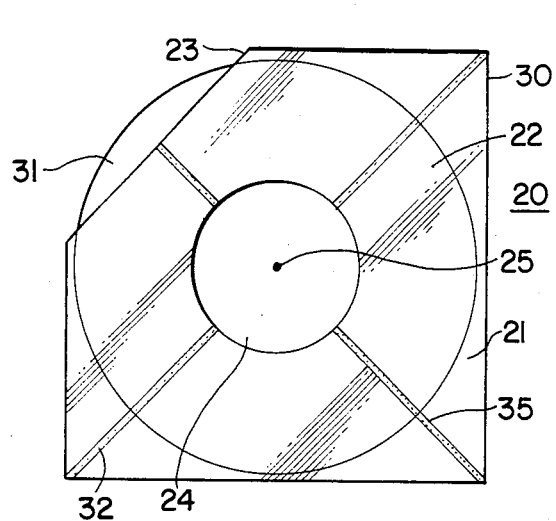
F I G. 2
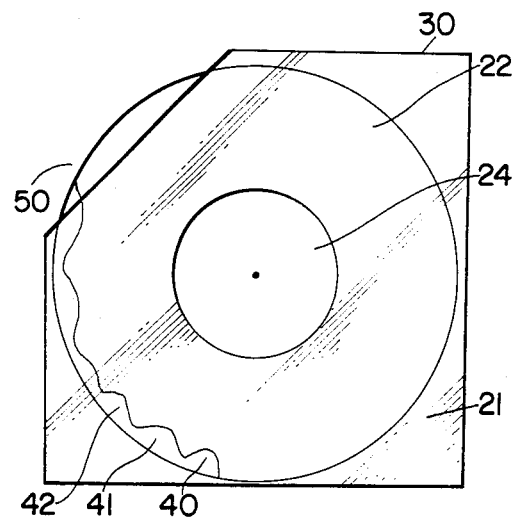
F I G. 3
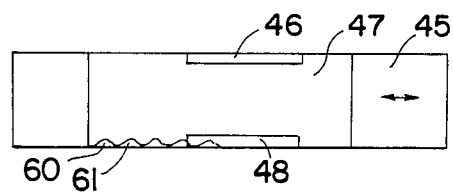
F I G. 4

MOVEABLE BLOTTER APPARATUS AND METHOD FOR USE IN BLEEDING-TIME TESTS

BACKGROUND OF THE INVENTION

The present invention relates to apparatus for use in bleeding-time tests and more particularly to a moveable blotter apparatus to enable a practitioner to perform a bleeding-time test in a rapid and reliable manner.

Bleeding time tests are performed to determine a patient's platelet activity. There are many devices that provide or produce skin incisions in the skin of a patient and are generally noted in the art. These devices are utilized to form a predetermined incision which incision is approximately 5 millimeters in length and 1 millimeter in depth. The bleeding time is defined as the time between implementing the incision and the moment the bleeding stops.

This is a well known test to determine the ability of blood platelets to stop bleeding from injured vessels. Such techniques have been described in the literature. Bleeding tests were first performed by surgeons or technicians who employed a scalpel to make an incision which was a relatively small incision at a relatively small depth. As indicated above, there are now devices which automatically perform such incisions at precise depth and at predetermined lengths. For example of such a device, reference is made to U.S. Pat. No. 4,643,189 issued on Feb. 17, 1987 and entitled APPARATUS FOR IMPLEMENTING A STANDARDIZED SKIN INCISION. This patent was awarded to Michael D. Mintz, the inventor herein.

As can be determined from that patent, there is shown a device which will implement a predetermined incision on the skin of a patient. In order to determine the bleeding time, the prior art utilized various items after the incision was implemented. The most commonly used item was an ordinary blotter or gauze type material which was placed near the incision and which was manipulated by the practitioner performing the test to determine the bleeding time. In this manner, the practitioner at 30 second intervals would hold the tissue or blotter near the incision making sure that the tissue or blotter did not touch the incision.

Blood from the wound would flow on to the material during the interval. During the next 30 seconds, a similar test was performed by holding an unused portion of the blotter or gauze again near the wound to determine whether blood was still flowing. This continued at 30 second intervals until the practitioner noted that blood flow had stopped thus ending the tests. The 30 second intervals indicative of the total of elapsed time in performing the test was implemented by means of a suitable timer or stop watch or conventional timing device.

This test is denoted as a bleeding-time test and is widely utilized prior to surgery and for many other reasons. As indicated, in order to accommodate such tests, the prior art practitioner utilized a conventional tissue, gauze or blotter or more fluid absorbing materials to determine whether or not bleeding had stopped. In any event, as one will immediately ascertain, in todays society there are many diseases such as AIDS which can be transmitted by body fluids. Hence, the prior art technique requires the strict use of gloves to prevent the practitioner from contacting or in any manner touching the blood flowing from the predetermined incision. As one can ascertain, by the use of such prior art devices—namely, sheets of paper or blotting materials and so on, the palm or other parts of the hand of a user could easily and oftentimes contact the blood during such procedures and as well as the fact that the blood on the material was uncovered and hence could be inadvertently contacted by anyone.

It is, therefore, an object of the present invention to provide a moveable blotter apparatus for use in bleeding-time tests which apparatus enables a practitioner to perform a bleeding-time test in a reliable and economical manner without exposing the practitioner to the blood.

It is a further object of the present invention to provide a moveable blotter apparatus having a blood absorbing material encased within a suitable envelope and having a portion protruding from the envelope wherein the blotter or blood absorbing material can be moved by the practitioner to change the protruded portion.

BRIEF DESCRIPTION OF THE PREFERRED EMBODIMENT

Apparatus for use in bleeding-time testing, comprising an envelope having an internal hollow and sealed at all sides, with an opening in at least one side, a blotter member located in said hollow of said envelope and dimensioned so that a peripheral section of said blotter extends from said opening, said envelope having a central aperture to enable a user to grasp said blotter member and to move said envelope with respect thereto to enable a different peripheral section of said blotter member to extend from said opening to enable a user to absorb blood from an incision at different peripheral sections of said blotter member with previous blots directed within the internal hollow of said envelope to thereby protect said user from contact with previously blotted blood.

BRIEF DESCRIPTION OF THE FIGURES

FIG. 1 is a perspective plan view depicting a patient's arm for describing operation of the apparatus according to this invention.

FIG. 2 is a front plan view of a rotatable blotter apparatus according to the invention.

FIG. 3 is a rear plan view of the apparatus depicted in FIG. 2.

FIG. 4 is an alternate embodiment of a moveable apparatus according to this invention.

DETAILED DESCRIPTION OF THE INVENTION

Referring to FIG. 1, there is shown an incision 10 which is implemented on the forearm of a patient. Such an incision is made by means of a suitable apparatus which is employed for implementing a standardized skin incision as for example described in the above-refereneced patent U.S. Pat. No. 4,643,189.

Once the incision 10 is implemented, the practitioner commences a timing interval which may be implemented by means of a stop watch 11 or any other suitable timing device. As indicated, a bleeding test is performed by monitoring the blood which oozes from the incision and determining when bleeding stops. Such monitoring occurs at 30 second intervals or other suitable intervals. When bleeding does stop, the end of the test is implemented.

As seen in FIG. 1, the practitioner whose arm is designated by numeral 21 holds the rotatable blotter apparatus 20 between his thumb and forefinger. The apparatus as will be further explained contains a transparent or clear envelope or housing 21 having contained therein a disk or a circular blotter member 22. The terms envelope and blotter are employed generically, and it is understood that different configurations can be employed. The circular blotter member 22 may be fabricated from different blotter materials or blood absorbing materials all of which are well known in the art. The envelope has a cut off corner opening 23 to allow a designated peripheral portion of the disk 22 to extend therefrom. The envelope also has a central aperture 24 to enable the practitioner to manipulate the device as will be explained.

In this manner, the exposed portion of the blotter is directed near the wound while the practitioner takes care that he does not touch the incision with the blotter, paper or filter paper 22. In any event, it is moved close to the incision so that blood 12 oozing from the incision acutually wets the blotter. As soon as a blood spot is essentially fully removed from the site by the absorbing action of blotter member 22, the unit 20 is removed from the wound and a new time period of 30 seconds is implemented. The practitioner by grasping the mechanism 20 as shown in FIG. 1 can rotate the disk 22 so that a new portion of the disk or blotter now protrudes from the cut off corner opening 23 to implement another 30 second test.

This process continues until there is no visual observation of the blood adhering to the most recently presented new peripheral portion of the exposed blotter thus terminating the test. In this manner, the practitioner can move the disk every 30 seconds approximately ⅜ of an inch to capture new blood under the influence of a timer. When no blood appears as indicative of a blot on the blotter disk 22, the practitioner determines the end of test and immediately operates his watch or timer device as 11 to indicate and determine the bleeding time. The practitioner can also view the blots through the transparent envelope, count the blots, and multiply the count by the time period to obtain a bleeding-test time.

The above-described device 20 is a relatively simple device, and reference is made to FIG. 2. The device 20 as indicated contains an outer envelope which may be fabricated from clear or transparent plastic. It is rectangular or square in shape but any other configuration can be implemented. It is sealed at all sides but has a corner slot or opening 23 to allow a peripheral portion of the blotter to extend therefrom. The envelope designated by reference numeral 21 has one corner 23 cut. Contained within the pouch or hollow of the envelope is a circular disk of blotting material designated by reference numeral 22. As indicated, the envelope includes a central aperture 24 which is symmetrically disposed and which permits access to the blotter disk 22. Thus, the practitioner can commence free turning of the disk within the envelope by holding his thumb and forefinger on opposite sides of the disk as close to the center 25 as possible. In this manner, the operator can grab a suitable corner such as corner 30 of the envelope and rotate the envelope with respect to the disk thereby causing a new portion of the disk as 31 to be provided. During rotation, the previously blotted section is directed into the envelope to avoid contact.

This can be accurately done. The lines such as lines 32 and 35 are shown in FIG. 2 to indicate that the plastic envelope is formed from a single sheet and then folded and secured at the lines. It is obvious how such plastic envelopes can be formed. The envelope material as indicated is a semi-rigid, preferably a transparent plastic sheet and which may be fabricate from acetate, PETG, vinyl and so on and is approximately 0.004 inches thick. The blotter material disk 22 is approximately 9 centimeters in diameter. The envelope is approximately 9.5×9.5 centimeters with the cut off corner 23 at an angle of 45° and 4 centimeters in length. These dimensions are only by way of example and other dimensions or shapes can be employed.

FIG. 3 shows the front view or opposite view of FIG. 2 indicating the aperture 24, the blotter material of disk 22, as well as the other surface of the envelope. As shown in FIG. 3, there is depicted a series of blots as 40, 41, and 42. Each blot was formed at a particular interval during the entire blood testing procedure. As one can ascertain from FIG. 3, each blot as formed on the disk enters the envelope 21 where it cannot in any manner be contacted or touched by the practitioner. The blot 40 would represent the first testing step, blot 41 the second, blot 42 the third testing step and so on. As one can ascertain, the blotter 22 is rotated with respect to the envelope 21 by the user grasping the blotter via the aperture 24 in the envelope and then by grabbing a corner such as corner 30 to rotate the envelope with respect to the disk so that a recent blot as for example blot 50 enters the envelope to thereby prevent contact of the same.

It is also understood as shown in FIG. 3 that a blot has a particular formation with a larger center area than at the sides. Hence, due to the transparent nature of the envelope 21, the practitioner can view the various blots as 40, 41, and 42 which are visually distinguishable and correlate the blood testing interval by the number of blots wherein each blot, for example, would represent a 30 second interval. In this manner, it is preferred that the envelope 21 be fabricated from a transparent plastic material, but it is, of course, understood that an opaque or any other material can be utilized as well. It is, of course, the main objective of the present invention to allow a practitioner to perform a blood test as indicated above without fear of contacting the absorbed blood which is being directed from the incision 10.

Referring to FIG. 4, there is shown an alternate embodiment of a moveable blotter apparatus according to this invention. In FIG. 4, the envelope 45 is again fabricated from a suitable transparent plastic material and is sealed at all sides. The envelope 45 has located within the internal hollow thereof a rectangular blotter member 47 which again is fabricated from materials as employed for blotter 22. The envelope has a top opening 46 and a bottom opening 48 both of which serve to expose a peripheral portion of the blotter member 47. As seen in FIG. 4, a user can grasp the blotter 47 by means of the aperture 46 and move the blotter 47 in a linear direction thereby causing a new peripheral portion of the blotter to appear at the bottom opening 48.

Hence, the operation of the above-described device is essentially similar to the device shown in FIGS. 2 and 3 and also allows previously blotted blood as 60 and 61 to be directed within the internal confines of the envelope. Again, due to the transparent nature of the envelope 45, a user can view the number of previous blots and correlate the bleeding time to such blots as described in conjunction with the appearance of FIGS. 2 and 3.

Hence as indicated above, the entire concept can employ many different geometrical configurations without depending from the main purpose of this invention which is to avoid contact with blotted blood during a bleeding time test procedure.

I claim:

1. Apparatus for use in bleeding-time testing, comprising:
   an envelope having an internal hollow and sealed at all sides, with an opening in at least one side,
   a blotter member located in said hollow of said envelope and dimensioned so that a peripheral section of said blotter extends from said opening, said envelope having an aperture to enable a user to grasp said blotter member and to move said envelope with respect thereto to enable a different peripheral section of said blotter member to extend from said opening to enable a user to absorb blood from an incision at different peripheral sections of said blotter member with previous blots directed within the internal hollow of said envelope to thereby protect said user from contact with said blotted blood.

2. The apparatus according to claim 1, wherein said envelope is fabricated from a transparent plastic material.

3. The apparatus according to claim 1, wherein said envelope is rectangular in shape and having said opening in one selected corner to allow access to said internal holow, with said blotter member being circular and dimensioned such that a peripheral segment extends from said one corner while enabling rotation of said blotter member with respect to said envelope.

4. The apparatus according to claim 1, wherein said envelope is rectangular in configuration having said opening on one side and having said aperture on another side with said blotter member being rectangular and contained within the hollow of said envelope.

5. The apparatus according to claim 1, wherein said aperture is a circular aperture.

6. The apparatus according to claim 1, wherein said envelope is fabricated from a plastic selected from acetate, PETG or vinyl.

7. A bleeding-test procedure where an incision is made in the skin of a patient and where the blood from said incision is directed onto an absorbing material at given intervals to determine when bleeding ceases during an interval as when blood does not emanate from said incision, with said intervals being timed to determine a bleeding time for said patient, the improvement comprising:
   employing an envelope having a peripheral opening and containing therein a blotter where said blotter is moved with respect to said envelope so that a new portion of said blotter is present at said opening to enable a user to perform said test by moving said blotter with respect to said envelope after each interval and to direct said blood as gathered by said blotter within said envelope to thereby avoid contact with the same.

8. The bleeding test procedure according to claim 7, wherein said envelope is rectangular having an opened corner and having a central aperture, with said envelope containing a circular blotter member with a peripheral portion extending from said opened corner and which is rotated by grasping said blotter via said aperture and turning said envelope to thereby change said extending peripheral portion while directing said blood blotted portion back into said envelope.

9. The bleeding-test procedure according to claim 5, wherein said incision is 5 mm in length and 1 mm in depth.

10. The bleeding-test procedure according to claim 7, wherein said user views previous blots via said transparent envelope to count said blots and multiply said count by said timed interval to obtain a bleeding-test time for said patient.

* * * * *